United States Patent
Yeh et al.

(10) Patent No.: US 10,633,628 B1
(45) Date of Patent: Apr. 28, 2020

(54) SYSTEMS FOR CULTIVATING AND DEWATERING ALGAE

(71) Applicants: Daniel H. Yeh, Tampa, FL (US); Ivy Lea Cormier Drexler, St. Petersburg, FL (US); Melanie Pickett, Tampa, FL (US); David Fulcher, Tampa, FL (US)

(72) Inventors: Daniel H. Yeh, Tampa, FL (US); Ivy Lea Cormier Drexler, St. Petersburg, FL (US); Melanie Pickett, Tampa, FL (US); David Fulcher, Tampa, FL (US)

(73) Assignee: University of South Florida, Tampa, FL (US)

( * ) Notice: Subject to any disclaimer, the term of this patent is extended or adjusted under 35 U.S.C. 154(b) by 258 days.

(21) Appl. No.: 15/350,582

(22) Filed: Nov. 14, 2016

Related U.S. Application Data (60) Provisional application No. 62/255,044, filed on Nov. 13, 2015.

(51) Int. Cl.
  *C12N 1/12* (2006.01)
  *C12M 1/00* (2006.01)
  *C12M 1/36* (2006.01)

(52) U.S. Cl.
  CPC ............. *C12N 1/12* (2013.01); *C12M 23/22* (2013.01); *C12M 29/04* (2013.01); *C12M 29/20* (2013.01); *C12M 41/48* (2013.01); *C12M 47/02* (2013.01)

(58) Field of Classification Search
  None
  See application file for complete search history.

(56) References Cited

U.S. PATENT DOCUMENTS 4,312,388 A * 1/1982 Hager ................. B65B 1/28
  141/1
8,033,047 B2 * 10/2011 Rasmussen ........... A01G 33/00
  47/1.4

(Continued)

OTHER PUBLICATIONS

Honda, et al., "Carbon dioxide capture and nutrients removal utilizing treated sewage by concentrated microalgae cultivation in a membrane photobioreactor," Bioresource Technology, 125 (2012) pp. 59-64 (Year: 2012).*

(Continued)

*Primary Examiner* — Chester T Barry
(74) *Attorney, Agent, or Firm* — Thomas | Horstemeyer, LLP (57) ABSTRACT

In one embodiment, an algae cultivation system includes a photobioreactor adapted for immersion in growth media contained within the growth media reactor, the photobioreactor including a closed container including multiple panels that together define an interior space in which algae can be cultivated, at least one of the panels being transparent, a porous membrane filter incorporated into one of the panels that enables water, carbon dioxide, and nutrients contained within the growth media to pass into the interior space but prevents contaminants contained within the growth media from passing into the interior space, and a gas control valve incorporated into one of the panels that when open enables photosynthetic gas produced by algae growth within the container to escape but when closed prevents the photosynthetic gas from escaping so as to build pressure within the container that forces water out from the container and dewaters the algae.

20 Claims, 4 Drawing Sheets

(56) References Cited

U.S. PATENT DOCUMENTS

| | | | |
|---|---|---|---|
| 8,399,239 B2 | 3/2013 | Zhang et al. | |
| 8,642,326 B1 | 2/2014 | Schaefer et al. | |
| 2009/0130706 A1* | 5/2009 | Berzin | C12M 21/02 435/41 |
| 2009/0137025 A1* | 5/2009 | Stephens | C12M 21/02 435/286.2 |
| 2011/0266215 A1 | 11/2011 | Robinson et al. | |
| 2012/0115210 A1 | 5/2012 | Winters et al. | |
| 2012/0135109 A1* | 5/2012 | Paeschke | A23L 2/02 426/50 |
| 2013/0232866 A1* | 9/2013 | Licamele | A01G 33/00 47/1.4 |
| 2016/0075981 A1* | 3/2016 | Lee | C12M 29/04 435/257.1 |
| 2018/0010082 A1* | 1/2018 | Jaques | B01F 7/00033 |

OTHER PUBLICATIONS

Barros, Ana, et al., "Harvesting Techniques applied to microalgae: A review", Renewable and Sustainable Energy Reviews 41, 1489-1500, 2015.

Lee, et al., "Fabric-Hydrogel Composite Membranes for Culturing Microalgae in Semipermeable Membrane-Based Photo bioreactors", Polymer Chemistry, Journal of Polymer Science, 54, 108-114, 2016.

* cited by examiner

SYSTEMS FOR CULTIVATING AND DEWATERING ALGAE

CROSS-REFERENCE TO RELATED APPLICATION

This application claims priority to U.S. Provisional Application Ser. No. 62/255,044, filed Nov. 13, 2015, which is hereby incorporated by reference herein in its entirety.

NOTICE OF GOVERNMENT-SPONSORED RESEARCH

This invention was made with Government support under Grant Number 1236746, awarded by the National Science Foundation. The Government has certain rights to the invention.

BACKGROUND

Algae are increasingly recognized as a renewable source of biofuel, but also have many other commercially valuable applications, such as pharmaceuticals, animal/fish feed, and fertilizers. However, there remain many problems in the large-scale production of algae, which hinder their economic competitiveness with other biofuel crops.

Algae are typically small in size (2-30 µm) and are cultivated in relatively dilute concentrations (generally less than 0.5 g dry biomass L-1), which makes harvesting and dewatering algal cultures particularly problematic and expensive. External inputs, such as nutrients, freshwater, and gases, also add a substantial environmental and economic burden. Wastewater, on the other hand, is a free source of nutrients, water, and carbon dioxide and, if utilized in algae production, could improve the economics and environmental footprint of large-scale algae production. However, utilizing wastewater may increase the chances of introducing predators, grazers, and invasive species to an algal culture, which can lead to algal culture collapse. As a case in point, open raceway ponds are easily contaminated by environmental contaminants (e.g., bacteria, fungi, and rotifers). Although synthetic growth media can be sterilized before it is added to a closed algal culture, this can add substantial cost to production.

From the above discussion, it can be appreciated that it would be desirable to have an alternative system and method with which algae can be cultivated, harvested, and dewatered.

BRIEF DESCRIPTION OF THE DRAWINGS

The present disclosure may be better understood with reference to the following figures. Matching reference numerals designate corresponding parts throughout the figures, which are not necessarily drawn to scale.

DETAILED DESCRIPTION

As described above, it would be desirable to have an alternative system and method with which algae can be cultivated, harvested, and dewatered. Examples of such systems and methods are disclosed herein. In some embodiments, the systems and methods include a photobioreactor that comprises a porous membrane filter that enables the passive transport of constituents (i.e., nutrients and gases) from a larger nutrient pool while still maintaining a physical barrier for potential competitors/predators/grazers or contaminants, such as endemic wastewater species, airborne pathogens, or bacteria/protozoans/metazoans, contained in the growth media. Separating the culture from the growth media precludes the need to sterilize the media, which saves energy and cost. In addition, the photobioreactor comprises a gas control valve that can be opened to vent gases generated during the cultivation of the algae from the photobioreactor and closed to contain the gases within the photobioreactor. When the gas control valve is closed, the gases collect in the headspace of the photobioreactor and force water out of the photobioreactor through the porous membrane filter so as to dewater the algae, thereby reducing energy and cost normally associated with algae production.

In the following disclosure, various specific embodiments are described. It is to be understood that those embodiments are example implementations of the disclosed inventions and that alternative embodiments are possible. All such embodiments are intended to fall within the scope of this disclosure.

This disclosure addresses issues of cultivation, harvesting, dewatering, and predator/grazer invasion in the production of algae. The disclosed systems and methods can be used with various types of growth media. The nutrients and carbon dioxide in the growth media, such as wastewater, can be used as a feedstock for algae production. In some embodiments, the disclosed systems employ porous membrane filters that enable such nutrients and carbon dioxide to reach the algae culture but restrict the passage of predators, grazers, and invasive species. The systems and methods, therefore, preclude the need to sterilize growth media prior to feeding it to the algal culture, thereby reducing costs. The porous membrane filter also prevents culture washout and retains the algal cells while still exposing them to fresh nutrients, which encourages higher cell density and eases harvesting and dewatering.

During photosynthesis, algae consume either dissolved carbon dioxide (an autotrophic reaction), dissolved organic carbon (a heterotrophic reaction), or a combination thereof (a mixotrophic reaction), and produce oxygen as a byproduct. Because oxygen has a lower water solubility than either carbon dioxide or dissolved organic carbon, it partitions readily into the gas phase. If such photosynthesis occurs in a photobioreactor in which gas-phase oxygen is not allowed to escape into the atmosphere (such as a closed bioreactor), then the accumulated oxygen in the headspace will generate a pressure in the headspace of the photobioreactor.

In addition to a porous membrane filter, the systems and methods comprise gas control valves that enable selective control over the photosynthetic gases, such as oxygen, that are produced as a byproduct of algae growth. More particularly, these gases can be selectively released or retained, as desired. When these gases are retained within the photobioreactor, the pressure increases within the cultivation space and water is evacuated through the porous membrane filter, thereby passively dewatering the algae prior to harvesting. This passive dewatering reduces downstream processing steps normally required in algae production and therefore improves the economic competitiveness of the entire process.

Figure 1:
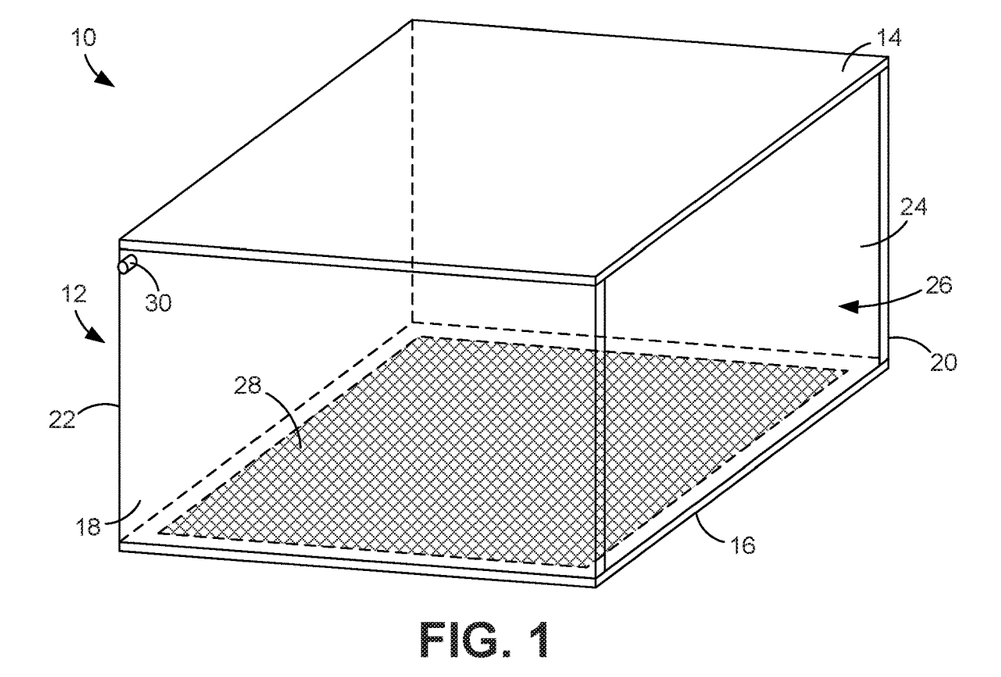
FIG. 1 is a perspective view of a first embodiment of a photobioreactor configured to enable controlled dewatering of algae cultivated within the photobioreactor.

FIG. 1 illustrates an embodiment of a photobioreactor 10 that can be incorporated into an existing or future algae cultivation system, stormwater pond, waste stabilization lagoon, wastewater reactor (e.g., aeration basin or settling clarifier), or other wastewater structure or waterway. As shown in FIG. 1, the photobioreactor 10 is configured as a generally rectangular container 12 that includes multiple generally planar wall panels. In the example of FIG. 1, these panels include a top panel 14, a bottom panel 16, a first end panel 18, a second end panel 20, a first side panel 22, and a second side panel 24. Each of these panels 14-24 can be generally perpendicular to each other to form an orthogonal rectangular box that defines an interior space 26. While an orthogonal rectangular box has been described and illustrated, it is noted that substantially any shape could be used, including three-dimensional polygons, cylinders, or hexagons. The particular shape that is used is not critical and may be influenced by various factors, such as the nature of the structure in which the photobioreactor 10 is to be used.

The size of the container 12 can be selected to suit the particular application in which it will be used. In some embodiments, however, the container 12 can have a length of approximately 1 to 10 m, a width of approximately 1 to 3 m, and a height of approximately 0.1 to 1 m, and the interior space 24 can have a volume of approximately 0.1 to 30 m$^3$. The container 12 can be transparent, or at least translucent, in which case the panels 14-24 can be made of a material that enables light, particularly sunlight, to easily pass through the panels. In some embodiments, the panels 14-24 are made of a clear polymeric material, such as an acrylic or polycarbonate material. Each of the panels 14-24 can be sealed along their shared edges to prevent ingress or egress of fluids. In some embodiments, one or more of the panels 14-24, such as the top panel 14, can be opened or removed from the container 12 to facilitate seeding of the container 12 and/or harvesting of algae from the container.

As can be appreciated from the above discussion, the container 12 includes a porous membrane filter 28. In the embodiment of FIG. 1, this porous membrane filter 28 is incorporated into the bottom panel 16. In particular, the bottom panel 16 comprises an opening that the porous membrane filter 28 covers. This membrane filter 28 enables water, gases (e.g., carbon dioxide and oxygen), and nutrients (e.g., nitrogen and phosphorus) to pass into the interior space 26 of the container 12, but prevents entry of contaminants and other unwanted components of the growth media into the space.

The parameters of the membrane filter 28, such as material, thickness, porosity, and permeability, can influence how the system functions and its selection is influenced by the overall goals of the system operation. Polymeric materials with a backing or cloth textile material having a pore size in the range of approximately 0.01 to 0.2 µm (20 to 350 kDa) may be preferable because they are durable and effective in precluding entry of potential biological contaminants. However, other membrane filter types could be utilized for projects with goals different than optimizing biomass productivity or culture protection. For example, if predation is less of a concern than the capital cost of the porous membrane filter photobioreactor infrastructure, a membrane filter with a pore size of 1 µm or greater could be used to reduce costs. However, with large pore sizes, seed culture may escape and predatory organisms may invade until a biological coating layer (biofilm) forms on the membrane filter surface. The membrane filter parameters may also influence constituent transport, which in turn affect overall productivity and/or algae metabolism. For example, if a project goal is to induce lipid production by restricting nitrogen, smaller membrane filter pores may be employed to retard the diffusion of nitrogen species across the membrane filter surface. In some embodiments, it is preferable that the pores of the membrane filter 28 are less than approximately 1 µm in size. By way of example, the pores can be in the range of approximately 0.01 to 0.2 µm (~20 to 350 kDa). In some cases, the membrane filter 28 can comprise an ultrafiltration membrane filter that forms part of a removable membrane filter cartridge that seals to bottom panel 16 of the container 12.

With further reference to FIG. 1, the photobioreactor 10 also comprises a gas control valve 30 that can be used to selectively release or retain gas generated within the container 12. As illustrated in this figure, the gas control valve 30 can be provided in one of the end or side panels 18-24 (panel 18 in FIG. 1) near a top end of the panel or in the top panel 14 so as to be located above a water line within the container and in fluid communication with a headspace of the container. As gas builds up within the container 12 due to photosynthetic gas production that occurs during algae cultivation, the gas can be vented from the container 12 when the gas control valve 30 is open and can be retained within the container when the gas control valve is closed. When the gas is retained within in the container 12, it collects in the headspace and increases in pressure. As the pressure increases, the gas displaces water from the container 12 through the porous membrane filter 28 so as to concentrate and dewater the algal culture. In some embodiments, the gas control valve 30 can be closed when the time for harvesting is approaching, for example, when the algae is nearing a desired density, age, or other relevant parameter. In other embodiments, the gas control valve 30 can be closed in the event that gas production (and therefore culture dewatering) is outpacing culture growth.

Irrespective of when the gas control valve 30 is closed, it can either be manually or electronically actuated. In the latter case, the gas control valve 30 can be a solenoid valve that opens or closes in response to an electrical signal delivered to a solenoid of the valve. When the gas control valve 30 is an electronically controlled valve, opening and closing of the valve can be automated. For example, a controller, such as a computer or other device having adequate computing power (e.g., microprocessor-based controller), can be programmed to automatically open and/or close the gas control valve 30 in response to certain detected conditions, such as the passage of a particular period of time or the sensing of a particular parameter of the algae that is indicative of it being time for dewatering.

In addition to controlling the release and retention of gas, the gas control valve 30 can also be used as a means for collecting gas to put to it use for other purposes, such as aeration in other processes or floatation of the photobioreactor.

Figure 2:
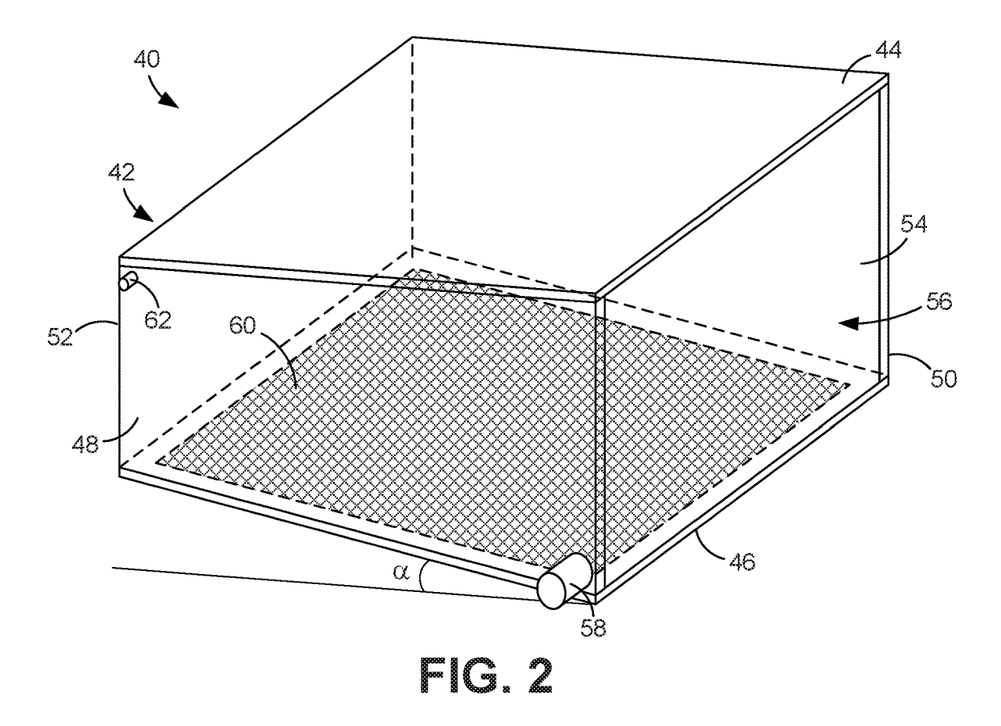
FIG. 2 is a perspective view of a second embodiment of a photobioreactor configured to enable controlled dewatering of algae cultivated within the photobioreactor.

FIG. 2 illustrates a further embodiment of a photobioreactor 40 that includes many of the features of the photobioreactor 10 shown in FIG. 1. The photobioreactor 40 is also configured as a generally rectangular container 42 that includes multiple generally planar wall panels, including a top panel 44, a bottom panel 46, a first end panel 48, a second end panel 50, a first side panel 52, and a second side panel 54. While the panels 44 and 48-54 can be generally perpendicular to each other as in the previous embodiment, the bottom panel 46 is tilted or slanted so as to form an angle α of declination with the horizontal plane that encourages collection of algae, via gravity, in a lowermost corner of the container 12 to facilitate harvesting. In some embodiments, the angle α is approximately 5 to 20 degrees. Like the container 12, the container 42 forms a box that defines an interior space 56, which can, for example, have a volume of approximately 0.1 to 30 m$^3$.

The container 42 can be transparent, or at least translucent, in which case the panels 44-54 are made of a material that enables light, particularly sunlight, to easily pass through the panels. In some embodiments, the panels 44-54 are made of a clear polymeric material, such as an acrylic material. Each of the panels 44-56 can be sealed along their shared edges to prevent ingress or egress of fluids. As with the container 12, one or more of the panels 44-54, such as the top panel 44, can be opened or removed from the container 42 to facilitate seeding of the container 42 and harvesting of algae from the container. In addition, however, the container 42 includes an algae extraction port 58 provided near the lowermost corner of the container (i.e., where the algae collects) that can be opened to facilitate removal of the algae that has been cultivated within the container 42. This algae can be pumped out of the container 42 through the extraction port 58. In some embodiments, the pressure of the gas that has been generated within the container 42 can at least assist in the evacuation of the algae from the container.

The container 42 also includes a porous membrane filter 60 that is incorporated into the bottom panel 46. In some embodiments, it is preferable that the pores of the membrane filter 60 are less than approximately 1 μm in size. By way of example, the pores can be in the range of approximately 0.01 to 0.2 μm (~20 to 350 kDa). In some cases, the membrane filter 60 can comprise an ultrafiltration membrane filter that forms part of a removable membrane filter cartridge that seals to bottom panel 46 of the container 42.

Like the photobioreactor 10, the photobioreactor 40 comprises a gas control valve 62 that can be used to selectively release or retain gas generated within the container 42. The gas control valve 62 can be provided in one of the end or side panels 48-54 (panel 48 in FIG. 2) near a top end of the panel or in the top panel 44 so as to be located above a water line within the container and in fluid communication with a headspace of the container. The gas control valve 62 can be manually or electronically actuated and, in the latter case, opening and closing of the valve can be automated, for example, using a suitable controller.

Figure 3:
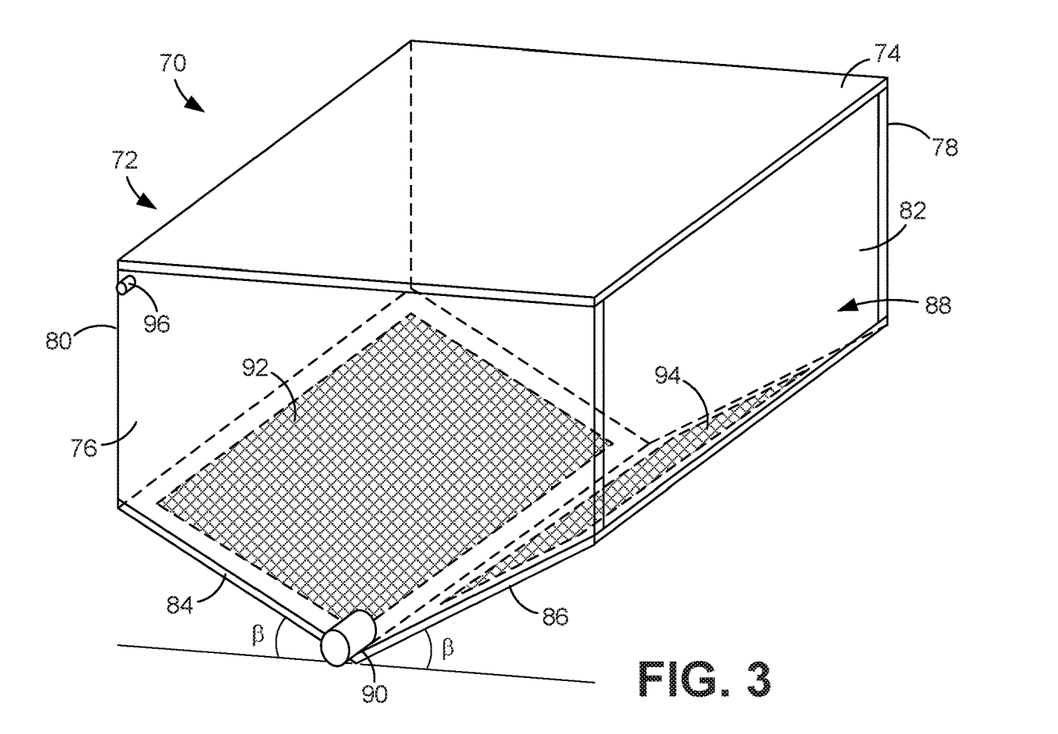
FIG. 3 is a perspective view of a third embodiment of a photobioreactor configured to enable controlled dewatering of algae cultivated within the photobioreactor.

FIG. 3 illustrates another embodiment of a photobioreactor 70 that includes features of both the photobioreactor 10 shown in FIG. 1 and the photobioreactor 40 shown in FIG. 2. The photobioreactor 70 is also configured as a generally rectangular container 72 that includes multiple generally planar wall panels, including a top panel 74, a first end panel 76, a second end panel 78, a first side panel 80, and a second side panel 82 that are generally perpendicular to each other. In this embodiment, however, the bottom of the container 72 comprises two tilted or slanted bottom panels 84 and 86 that together define a V-shaped trough in which cultivated algae can settle. By way of example, each of the bottom panels 84, 86 forms an angle β of declination with the horizontal plane that ranges from approximately 5 to 20 degrees. Like the container 12, the container 72 forms a box that defines an interior space 88, which can, for example, have a volume of approximately 0.1 to 30 m$^3$.

The container 72 can be transparent, or at least translucent, in which case the panels 74-86 is made of a material that enables light, particularly sunlight, to easily pass through the panels. In some embodiments, the panels 74-86 are made of a clear polymeric material, such as an acrylic material. Each of the panels 74-86 can be sealed along their shared edges to prevent ingress or egress of fluids. As with the container 12, one or more of the panels 74-86, such as the top panel 74, can be opened or removed from the container 72 to facilitate seeding of the container and harvesting of algae from the container. In addition, the container 72 includes an algae extraction port 90 located near the bottom of the trough that can be opened to facilitate removal of the algae that has been cultivated within the container 72. This algae can be pumped out of the container 72 through the extraction port 90 and, in some embodiments, the pressure of the gas that has been generated within the container 72 can at least assist in the evacuation of the algae from the container.

The container 72 also includes porous membrane filters 92 and 94 incorporated into the bottom panels 84 and 86, respectively. In some embodiments, it is preferable that the pores of the membrane filters 92, 94 are less than approximately 1 μm in size. By way of example, the pores can be in the range of approximately 0.01 to 0.2 μm (~20 to 350 kDa). In some cases, the membrane filters 92, 94 can comprise ultrafiltration membrane filters that form part of a removable membrane filter cartridge that seals to the bottom panels 84, 86.

The photobioreactor 70 further comprises a gas control valve 96 that can be used to selectively release or retain gas generated within the container 72. The gas control valve 96 can be provided in one of the end or side panels 76-82 (panel 76 in FIG. 3) near a top end of the panel or in the top panel 74 so as to be located above a water line within the container and in fluid communication with a headspace of the container. The gas control valve 96 can be manually or electronically actuated and, in the latter case, opening and closing of the valve can be automated, for example, using a suitable controller.

Figure 4:
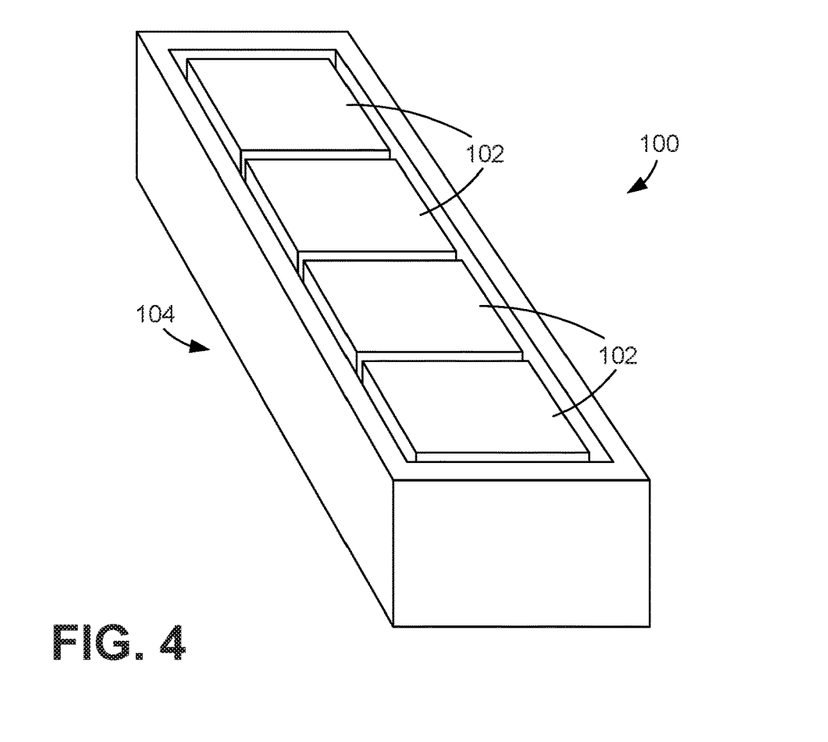
FIG. 4 is a perspective view of an algae cultivation system that includes multiple photobioreactors.

Porous membrane filter photobioreactors of the types shown in FIGS. 1-3 can be deployed in a growth media reactor to form an algae cultivation system 100, as shown in FIG. 4. In particular, one or more photobioreactor containers 102 can be placed within an outdoor, open-topped growth media reactor 104 that contains growth media, such as wastewater. The containers 102 can be positioned within the reactor 104 such that the top panels of the containers are positioned above the surface of the growth media while the other panels are completely or nearly completely immersed in the media. The depth at which the containers 12 are immersed can vary with the volume of algae culture that is produced. The containers 12 can either float within the growth media using floats (not shown) connected to the containers, and/or can be tethered to the walls of the reactor 104 with tethers (not shown). When the containers 102 are correctly positioned within the reactor 104, the growth media within the reactor can pass through the porous membrane filters of the containers 102 and enter their interior spaces. Prior to immersion in the growth media 32, the photobioreactor containers 12 can be seeded with algal cells of the target algae species that is to be cultivated. When the containers 12 are exposed to light, particularly sunlight, the algae will then grow within the containers.

In some embodiments, the porous membrane filter photobioreactor containers 102 can be manually or automatically extracted from the reactor 104 for harvesting. In such a case, one of the container panels (e.g., the top panel) can be removed to access the container's interior space and the algal culture will settle at the bottom of the container 102. Residual water can be drained through the membrane filters and any remaining water can be poured out of the containers and, if desired, retained for later seeding purposes. The algal culture can then be scraped from the membrane filters and placed in an appropriate collection vessel. The outer surfaces of the container panels can be cleaned and the interior spaces can be reseeded. Once reseeding has been performed, the removed panels can be replaced and the containers 102 can be returned to the reactor 104.

In cases in which the containers 102 comprise algae extraction ports, the algae that has collected at the bottoms of the containers can be removed via the extraction ports. As noted above, this extraction can be performed using a pump and the increased pressure resulting from gas generation within the container 102 may assist in the extraction (or ejection) process. In some embodiments, each of multiple containers 102 can be connected in series or parallel to form a network, for example with pipes or tubes, such that the interior spaces of each container are in fluid communication with each other when the extraction ports are open. In such a case, algae can be extracted from the interior spaces of multiple containers by connecting to a single one of the containers.

Figure 5A:
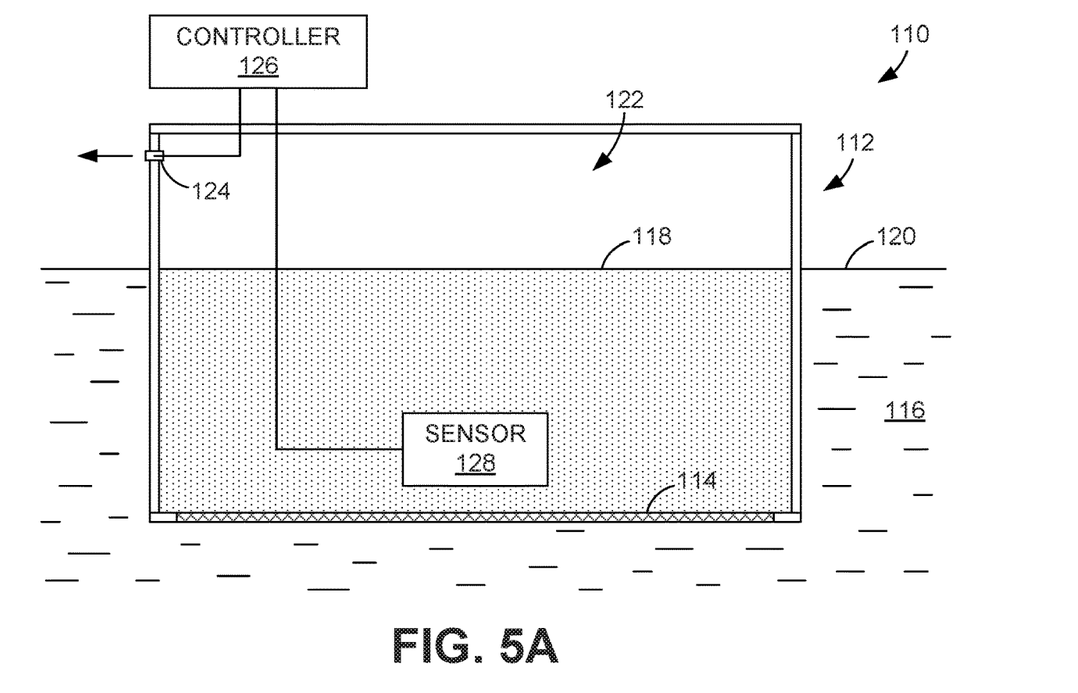
FIGS. 5A and 5B are end views of a photobioreactor illustrating controlled dewatering of algae within the photobioreactor.
Figure 5B:
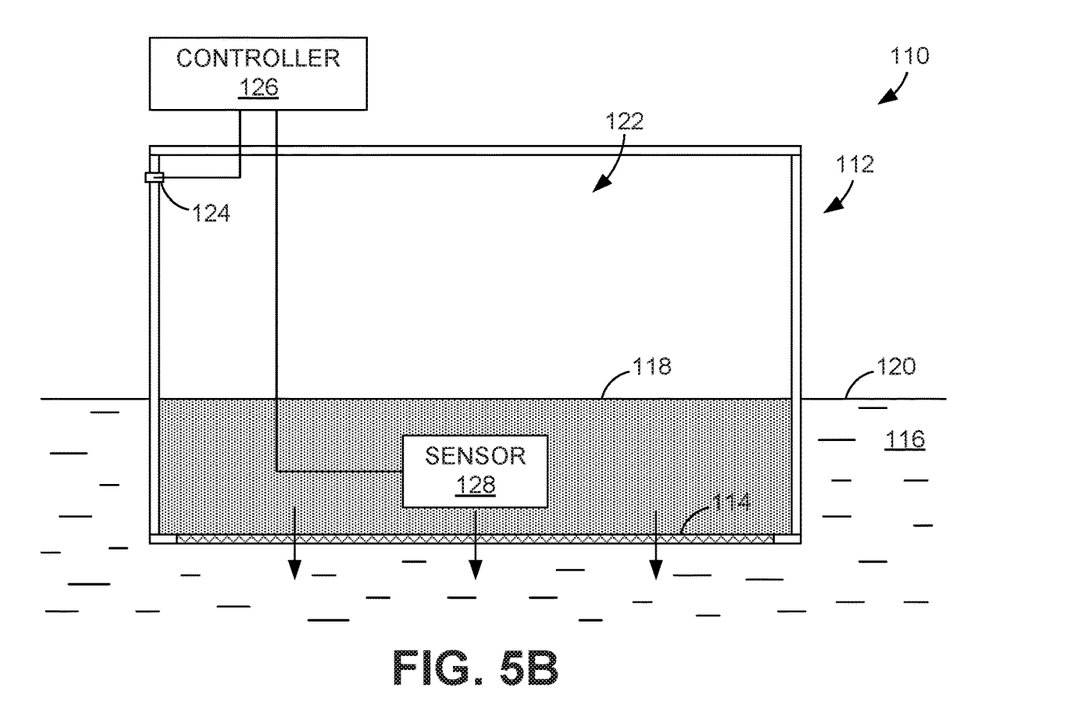

As noted above, the gas control valve of a photobioreactor can be used to selectively dewater the algae that has been cultivated in the photobioreactor prior to harvesting. FIGS. 5A and 5B illustrate such a process. As shown in these figures, a photobioreactor 110 includes a container 112 comprising a porous membrane filter 114. While the container 112 has a configuration similar to that shown in FIG. 1, this container is merely exemplary. The container could, for example, have a configuration shown in FIG. 2 or 3. The container 112 is partially immersed in a water-based growth media 116, which may comprise wastewater. Because of the presence of the porous membrane filter 114, water can enter the container 112. In an initial state shown in FIG. 5A in which algae is beginning to grow, this water fills the container to a point at which the surface 118 of the water within the container 112 is generally equal to the surface 120 of the growth media 116 in which the container is immersed. As the algae grows, photosynthetic gas, such as oxygen, is generated by the growth of the algae and rises to a headspace 122 within the container 112 above the surface 118 of the water within the container 112. During this time, the gas control valve 124 can be left open to enable this gas to escape from the container 112. In some embodiments, this gas can be collected and stored for later use.

FIG. 5B shows the photobioreactor later in the algae cultivation process. At this point in the process, a substantial amount of algae has grown and this algae is nearly ready for harvesting (e.g., nearing a desired density, age, or other relevant parameter). Prior to performing this harvesting, it may be desirable to dewater the algae. To do this, the gas control valve 124 is closed to retain the gas that is produced by the algae growth. As this gas fills the headspace, it pressurizes the container 112 to the point at which water is forced out of the container through the porous membrane filter 114. As this happens, the surface 118 of the water within the container 112 drops with respect to the container wall, (i.e., the container rises with respect to the growth medium surface 120) and the algae is concentrated (i.e., dewatered) at the bottom of the container. This algae may be in the form of an algal slurry that can be pumped out of the container 112 during harvesting. Furthermore, the extent to which the container 112 rises with respect to surface 120 can be used as an external indication (visual or measured) of the extent of photosynthetic activity and consequent dewatering that has occurred.

As described above, the dewatering process can be automated. In particular, when the gas control valve 124 can be electrically actuated, a suitable controller can automatically open or close the control valve at the appropriate times. FIGS. 5A and 5B identify such a controller 126, which can comprise a computer or a microprocessor-based controller. In some embodiments, the controller 126 can be configured to close the control valve 124 and initiate dewatering at a particular time after the photobioreactor 110 has been seeded and immersed in the growth media 116. In other embodiments, the controller 126 can close the control valve 124 in response to a signal received by a sensor 128 that is configured to sense a parameter indicative of the algae reaching a state at which dewatering should be performed. By way of example, the sensor 128 can comprise an optical sensor, a density sensor, a pressure sensor, temperature sensor, a chlorophyll sensor, a nutrient/ion sensor, a dissolved gas sensor, a turbidity sensor, or combinations thereof. In other embodiments, the sensor can comprise a head-space temperature, pressure, or gas flow sensor that can be used to monitor the rate or cumulative volume of gas exiting the container 112 through the open gas control valve 124. Irrespective of the nature of the sensor or the parameter(s) it senses, the controller 126 can monitor the parameters and, when a parameter is reached that indicates that dewatering and harvesting should be performed, the controller can send an electrical signal to the gas control valve 124 that causes it to close.

It is also noted that the gas control valve 124 can be used to periodically clear the membrane filter 114 without the need to remove the container 112 from the growth media. Specifically, the gas control valve 124 can be closed to enable gas to collect within the headspace 122 of the container 112 and force water out of the container. Once an appropriate volume of water has been displaced, the gas control valve 124 can be suddenly opened to enable water to flow back into the container 112 through the porous membrane filter 114. This flow may clear algae from the inside surface of the membrane filter 114 that would otherwise clog the filter and inhibit the passage of nutrients and carbon dioxide into the container 112.

As noted above, the gas produced within the container 112 can be collected for other use. For example, photosynthetic oxygen may be used in other aerobic processes (e.g., wastewater treatment, aquaculture). In addition or exception, the gas can be used to inflate floats (not shown) mounted to the container 112, which can be used to control the position of the container within the growth medium (taking advantage of passive dewatering) or to elevate one side of the photobioreactor to encourage concentrated settling.

Figure 6:
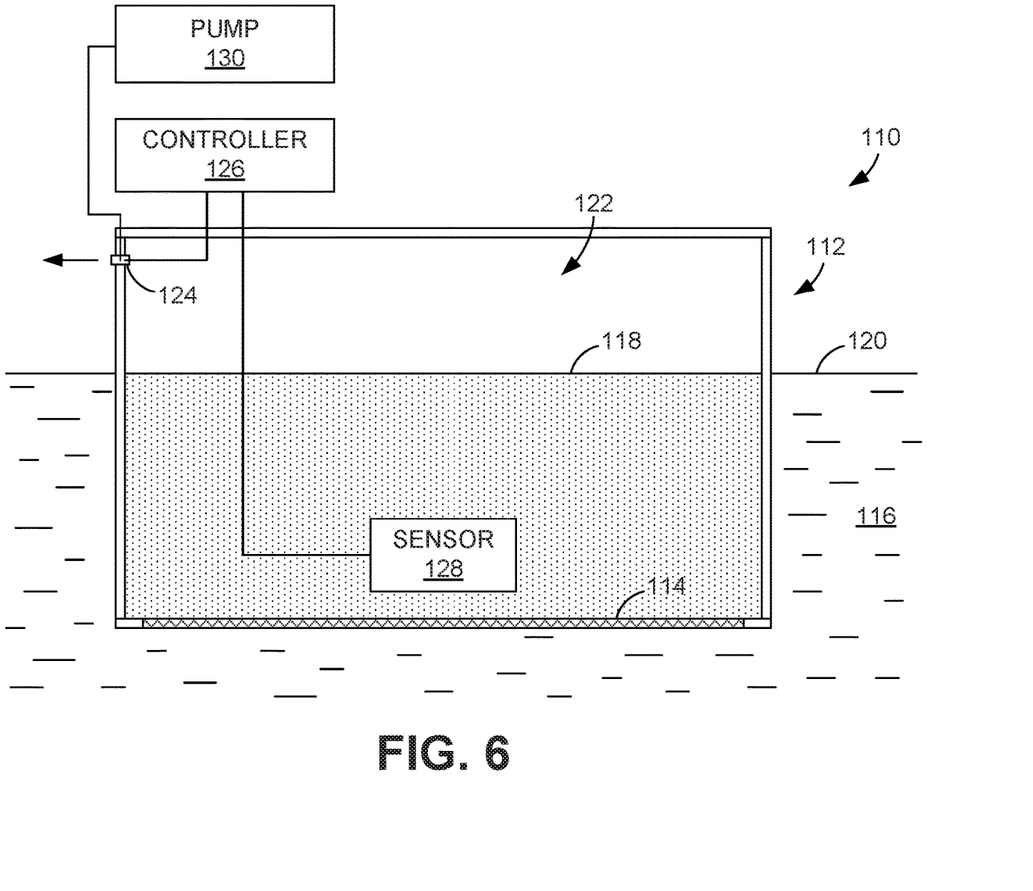
FIG. 6 is an end view of a photobioreactor including a pump that can be used to pressurize or depressurize the headspace of the photobioreactor.

While the gas control valve 124 can be simply opened or closed to regulate the pressure of the gas within the headspace 122 of the container 112, alternatively or additionally, this pressure can be regulated using a pump. FIG. 6 illustrates such an embodiment. In this embodiment, a pump 130 can be used to deliver gas to or remove gas from the headspace 122 via the gas control valve 124. When gas is removed from the headspace 122 using the pump 130, the growth medium 116 can be drawn into the container 112 through the membrane filter 114. This serves the functions of dislodging accumulated algae from the filter surface and actively drawing in fresh growth constituents (e.g., carbon dioxide and nutrients) into the photobioreactor 110 to replenish depleted growth constituents at a rate higher than diffusion alone would enable, thereby enabling algae to grow faster. When gas, such as air, is pumped into the container 112, the gas will push water out of the photobioreactor 110 at a faster rate than photosynthetic dewatering would alone. This approach offers additional control over dewatering. In addition, it accelerates the rate of dewatering, increases the extent of dewatering, enables precise control on dewatering event in terms of the timing (onset, and duration) of the event, and provides a backup to photosynthetic dewatering.

The invention claimed is:

1. An algae cultivation system comprising:
a growth media reactor that contains growth media; and
a photobioreactor at least partially immersed in the growth media of the growth media reactor, the photobioreactor comprising a container including multiple panels that together define an interior space in which algae can be cultivated, at least one of the panels being transparent, wherein a bottom panel includes a porous membrane filter having pores approximately 0.01 to 0.2 µm in size that enables water, carbon dioxide, and nutrients contained within the growth media to pass into the interior space but prevents contaminants contained within the growth media from passing into the interior space;
a sensor provided within the container configured to sense a parameter of the algae that is indicative of when the algae is ready for harvesting;
an electronically actuated gas control valve associated with one of the container panels configured to be selectively opened and closed, wherein when the gas control valve is open the valve enables photosynthetic gas produced by algae growth within the container to escape but when the gas control valve is closed the valve prevents the photosynthetic gas from escaping so as to build pressure within the container that forces water out from the container through the porous membrane filter and dewaters the algae; and
a controller in electrical communication with the sensor and the gas control valve, the controller being configured to receive signals from the sensor and, when the signals indicate that the algae is ready for harvesting, close the gas control valve to dewater the algae to prepare it for harvesting.

2. The system of claim 1, wherein the growth media reactor is an outdoor, open-top growth media reactor.

3. The system of claim 1, wherein the photobioreactor comprises multiple transparent panels made of a clear polymeric material.

4. The system of claim 1, wherein the container includes a bottom panel that is slanted so as to form an angle with a horizontal plane.

5. The system of claim 1, wherein the container includes two bottom panels that are slanted so as to form a V-shaped trough in which algae can settle.

6. The system of claim 1, wherein the photobioreactor further comprises an algae extraction port through which dewatered algae can be removed from a bottom of the container.

7. The system of claim 1, wherein the sensor comprises one of an optical sensor, a density sensor, a pressure sensor, a temperature sensor, a chlorophyll sensor, a nutrient/ion sensor, a dissolved gas sensor, a turbidity sensor, a gas flow sensor, or a combination thereof.

8. The system of claim 1, wherein the electronically actuated gas control valve comprises a solenoid valve.

9. The system of claim 1, further comprising a pump configured to regulate gas pressure within the container.

10. The system of claim 9, wherein the pump is configured to alternatively deliver gas to and remove gas from the container.

11. A photobioreactor adapted for immersion in growth media contained within a growth media reactor, the photobioreactor comprising:
a container including multiple panels that together define an interior space in which algae can be cultivated, at least one of the panels being transparent;
a porous membrane filter having pores approximately 0.01 to 0.2 µm in size incorporated into a bottom panel of the container that enables water, carbon dioxide, and nutrients contained within the growth media to pass into the interior space but prevents contaminants contained within the growth media from passing into the interior space;
a sensor provided within the container configured to sense a parameter of the algae that is indicative of when the algae is ready for harvesting;
an electronically actuated gas control valve incorporated into one of the panels of the container configured to be selectively opened and closed, wherein when the gas control valve is open the valve enables photosynthetic gas produced by algae growth within the container to escape but when the gas control valve is closed the valve prevents the photosynthetic gas from escaping so as to build pressure within the container that forces water out from the container and dewaters the algae; and
a controller in electrical communication with the sensor and the gas control valve, the controller being configured to receive signals from the sensor and, when the signals indicate that the algae is ready for harvesting, close the gas control valve to dewater the algae to prepare it for harvesting.

12. The photobioreactor of claim 11, wherein the photobioreactor comprises multiple transparent panels.

13. The photobioreactor of claim 12, wherein the transparent panels are made of a clear polymeric material.

14. The photobioreactor of claim 11, wherein the container includes a bottom panel that is slanted so as to form an angle with a horizontal plane.

15. The photobioreactor of claim 11, wherein the container includes two bottom panels that are slanted so as to form a V-shaped trough in which algae can settle.

16. The photobioreactor of claim 11, further comprising an algae extraction port through which dewatered algae can be removed from a bottom of the container.

17. The photobioreactor of claim 11, wherein the sensor comprises one of an optical sensor, a density sensor, a pressure sensor, a temperature sensor, a chlorophyll sensor, a nutrient/ion sensor, a dissolved gas sensor, a turbidity sensor, a gas flow sensor, or a combination thereof.

18. The photobioreactor of claim 11, wherein the electronically actuated gas control valve comprises a solenoid valve.

19. The photobioreactor of claim 11, further comprising a pump configured to regulate gas pressure within the container.

20. The photobioreactor of claim 19, wherein the pump is configured to alternatively deliver gas to and remove gas from the container.

\* \* \* \* \*